US010278386B2

(12) United States Patent
Ward et al.

(10) Patent No.: US 10,278,386 B2
(45) Date of Patent: May 7, 2019

(54) SOLUTIONS FOR ENHANCING THE EFFECTIVENESS OF INSECTICIDES AND FUNGICIDES ON LIVING PLANTS AND RELATED METHODS

(71) Applicant: KOP-COAT, INC., Pittsburgh, PA (US)

(72) Inventors: Hans A. Ward, Wexford, PA (US); Ronald Walton Clawson, Jr., Monroeville, PA (US); Kenneth Allen Cutler, Verona, PA (US); Cameron R. Scott, Rotorua (NZ)

(73) Assignee: KOP-COAT, INC., Pittsburgh, PA (US)

( * ) Notice: Subject to any disclaimer, the term of this patent is extended or adjusted under 35 U.S.C. 154(b) by 0 days.

(21) Appl. No.: 15/079,478

(22) Filed: Mar. 24, 2016

(65) Prior Publication Data
US 2016/0286795 A1    Oct. 6, 2016

Related U.S. Application Data

(62) Division of application No. 14/674,465, filed on Mar. 31, 2015.

(51) Int. Cl.
| | | |
|---|---|---|
| *A01N 25/30* | (2006.01) | |
| *A01N 33/24* | (2006.01) | |
| *A01N 43/653* | (2006.01) | |
| *A01N 53/00* | (2006.01) | |

(52) U.S. Cl.
CPC ............. *A01N 25/30* (2013.01); *A01N 33/24* (2013.01); *A01N 43/653* (2013.01); *A01N 53/00* (2013.01)

(58) Field of Classification Search
USPC ....................................................... 514/383
See application file for complete search history.

(56) References Cited

U.S. PATENT DOCUMENTS

| | | | |
|---|---|---|---|
| 4,474,597 A * | 10/1984 | Schmidt ................. | A01N 47/16 504/138 |
| 5,710,103 A | 1/1998 | Magin et al. | |
| 5,833,741 A | 11/1998 | Walker | |
| 5,846,305 A | 12/1998 | Payzant | |
| 6,274,199 B1 | 8/2001 | Preston et al. | |
| 6,306,850 B1 * | 10/2001 | Dutzmann ............. | A01N 43/653 514/229.2 |
| 6,340,384 B1 | 1/2002 | Walker | |
| 6,375,727 B1 | 4/2002 | Walker | |
| 6,416,789 B1 * | 7/2002 | Marks .................... | A01N 47/12 424/617 |
| 6,448,279 B1 | 9/2002 | Tseng et al. | |
| 6,508,869 B2 | 1/2003 | Tseng et al. | |
| 6,527,981 B1 * | 3/2003 | Tseng .................. | A01N 43/653 106/18.32 |
| 6,572,788 B2 | 6/2003 | Walker | |
| 6,811,731 B2 | 11/2004 | Archer et al. | |
| 7,056,919 B2 | 6/2006 | Ross et al. | |
| 7,655,281 B2 | 2/2010 | Ward et al. | |
| 7,896,960 B2 | 3/2011 | Ward et al. | |
| 2002/0065206 A1 | 5/2002 | Tseng et al. | |
| 2005/0008576 A1 | 1/2005 | Makansi | |
| 2009/0062127 A1 | 3/2009 | Liu | |
| 2009/0088481 A1 | 4/2009 | Ward et al. | |
| 2012/0258248 A1 * | 10/2012 | Ross .................... | B27K 3/0285 427/337 |
| 2013/0172184 A1 | 7/2013 | Bain et al. | |
| 2014/0235445 A1 | 8/2014 | Sanders | |

FOREIGN PATENT DOCUMENTS

| | | | |
|---|---|---|---|
| EP | 1273234 A1 | 1/2002 | |
| EP | 2473035 A2 | 7/2012 | |
| EP | 2615921 A1 | 7/2013 | |
| WO | WO 0071314 | * 11/2000 | ............... B27K 3/50 |
| WO | WO2013189777 A1 | 12/2013 | |
| WO | WO2014191096 A1 | 12/2014 | |

OTHER PUBLICATIONS

Mueller et al. Fungicides: Why fungicides fail, on pp. 180181 of the Integrated Crop Management, 496 (16) Jun. 19, 2006.*
McGrath, M.T. 2004. What are Fungicides. The Plant Health Instructor. DOI: 10.1094/PHII2004082501.*
Fishel et al. pH and the Effectiveness of Pesticides, Purdum, E.D. 2002.*
Shilder et al. 2012 http://msue.anr.msu.edu/news/how to get the most out of your fungicide sprays on fruit crops.*
Robinson, 2006 North Central Weed Science Society. 61:140.*
Kleszczynskaa, 2005 Verlag der Zeitschrift für Naturforschung, Tübingen.*
Cynthia Ocamb, Sep. 2010, Fungicide Groups, Modes of Action & Effective Pathogen Control.*
Alan Wood, Frac Code, Dec. 2005.*
Berg, 1986, Green and Spilker, Fungicide Chemistry, ACS Symposium Series, Washington DC.*
Red List, Numbers of threatened species by major groups of organisms (1996-2010).*
Bartlett, Pesticide Outlook—Aug. 2001.*
Grower Talks, Insecticide and Funcgicide Guide, 2014-2015.*
FRAC Code List © *2018: Fungicides sorted by mode of action (including FRAC Code numbering).*
Label for Warrior™ Dandelion and Weed Killer Concentrate.
Label for Roundup® Weed and Grass Killer Concentrate.
Andrew D. Malec, et al. Improving Water Soluble Agricultural Formulations With Amine Oxides, Proc. ISAA 2013, pp. 85-89.

* cited by examiner

*Primary Examiner* — Nizal S Chandrakumar
(74) *Attorney, Agent, or Firm* — Eckert Seamans Cherin & Mellott, LLC; Arnold B. Silverman

(57) ABSTRACT

The present invention relates to a solution for resisting destruction of living plants and a related method. A solution including a buffered amine oxide admixed with at least one material selected from the group consisting of insecticides and fungicides is applied to the living plant and provides a synergistically effective greater resistance to living plant deterioration than any of the individual buffered amine oxide, insecticides and fungicide achieve considered individually. A related method is disclosed.

15 Claims, No Drawings

SOLUTIONS FOR ENHANCING THE EFFECTIVENESS OF INSECTICIDES AND FUNGICIDES ON LIVING PLANTS AND RELATED METHODS

BACKGROUND OF THE INVENTION

1. Field of the Invention

The present invention relates to an improved solution for enhancing protection of living plants through synergistic effects between buffered amine oxides and insecticides and fungicides and related methods.

2. Description of the Prior Art

Fungi, insects and other pests cause significant economic losses in food crop production as well as losses in forestry, tree plantations, pastures, flowers and other agricultural products. In addition, fungicide and insecticides have been employed in a wide variety of locations and types of uses to inhibit plant destruction due to fungus and insect pests. Problems created by insects and fungi have long existed in many environments including, but not limited to agriculture, parks, golf courses, residential environments, highways, vegetable gardens, railroad tracks, recreational facilities, floral gardens, forests, pastures, waterways and in many other environments. This can interfere with desired functionality, the health of plants, as well as the aesthetics of an area containing vegetation.

It has been known to use a wide variety of materials to protect living plants from insects and fungi. A wide variety of insecticides and fungicides have been employed in order to enhance the health of living plants and resist attack thereon by insects, fungi and other destructive organisms.

It has been known to introduce wood preservatives into lumber in order to resist deterioration of the same.

Ward, U.S. Pat. No. 7,896,960 discloses a method and solution for providing enhanced penetration of wood preservatives into wood to a greater depth through synergism between a buffering agent and an amine oxide. It contemplates the use of various types of wood preservatives on wood which has been severed from a living tree. Green lumber is also said to be treatable by the system.

This patent, which relates to wood as distinguished from living plants does include within the definition of wood preservatives, a number of chemical compounds including specific reference to fungicidal, insecticidal, water resistant, termite resistant materials.

U.S. Pat. No. 6,811,731 is directed toward a fire-retardant wood-based composite created by treating a green wood furnish with a phosphate/borate fire-retardant material. The fire-retardant treated green wood furnish is blended with a binder and then bound by applying pressure to form a non-leaching fire retardant wood based composite.

Walker, U.S. Pat. No. 6,572,788 discloses the use of amine oxides as wood preservatives. It states that the amine oxides inhibit microbial growth in wood. This patent relates to wood which has been severed from growing trees and discloses the use of wood preservatives which are said to inhibit destructive organisms such as fungi and sapstain, for example. It is directed toward preserving structural integrity of wood after the tree has been killed and resisting destruction of the resultant lumber as the prime objective.

Tseng, U.S. Pat. No. 6,508,869 discloses the use of amine oxides to enhance the performance of boron compounds as wood preservatives. There is mention of the amine oxides improving the effectiveness of boron compounds as insecticides or biocides and plant growth regulating agents. They are also said to provide better dispersion of boron compounds when applied to plants and fungi. It also makes reference to the seeds of plants and the area on which the plants or fungi grow.

There remains, therefore, a very real and substantial need for an improved system for resisting attacks on and destruction of living plants by insects and fungi.

SUMMARY OF THE INVENTION

The present invention provides a solution and method of obtaining synergistic action between a fungicide and a buffered amine oxide and/or an insecticide and a buffered amine oxide in order to provide enhanced resistance of a living plant to undesired deterioration due to fungi and insects.

The solution and related method provides for greater plant protection than would be obtained through use of the fungicide alone or the insecticide alone.

It is an object of the present invention to provide effective economical means for enhancing the performance of insecticides and fungicides on living plants.

It is another object of the present invention to provide a solution and related method which will enhance the performance of fungicides and insecticides on living plants.

It is another object of the present invention which, through synergism with a buffered amine oxide, enhances the performance of conventional insecticides and fungicides.

It is yet another object of the present invention to employ a synergistic combination of insecticides or fungicides with a buffered amine oxide system to produce improved insect and fungi resistance while employing a smaller quantity of the insecticide or fungicide.

These and other objects of the invention will be more fully understood from the following description of the invention.

DESCRIPTION OF THE PREFERRED EMBODIMENTS

As employed herein, the term "living plant" is used in its ordinary sense, and is to be distinguished from both (a) plants which have died and (b) products or items which once were, but are no longer living or part of a living plant such as, for example, lumber. This definition will include living plant food products such as fruits or vegetables which have been removed from a plant.

As employed herein, a "buffer system" is an aqueous solution consisting of a mixture of a weak acid and its conjugate base or a weak base with its conjugate acid. A buffer system may also be obtained by adding a weak acid/conjugate base or a weak base/conjugate acid or by adding the weak acid/weak base and a strong acid/strong base in sufficient amount to form the conjugate acid/conjugate base.

The present invention involves creating a synergistic effect by applying to the plant a solution which includes of either an insecticide or a fungicide or both which will achieve a synergistically created improvement in the result through combining the same with a buffered amine oxide.

The amine oxides may be mixed with buffers in a solvent to create a buffered amine oxide solution and then mixed with a herbicide solution. The preferred amine oxides are selected from the group consisting of (a) the 12 carbon length amine oxides such as that sold under the trade designation Barlox 12 and (b) a mixture of the 12 and 18 carbon lengths sold under the trade designation Barlox 1218. The buffer system has the property that the pH of the solution changes very little when a small amount of a strong acid or strong base is added to it. Buffer solutions are employed as a means of keeping pH at a nearly constant value within a wide range of chemical operations. In the present invention, the buffer system helps to maintain a substantially constant pH when in contact with biological systems, such as living plants.

The buffer system concepts can be extended to polyprotic species in which one or more protons may be removed to form different buffer systems, i.e., phosphate systems. Among the preferred buffers are ammonium salt/ammonia, Deprotonated Lysine/Doubly Deprotonated Lysine, Phosphate Dibasic, Potassium Bicarbonate/Potassium Carbonate.

Boric Acid/Borax, Potassium Phosphate Dibasic/Potassium Phosphate Tribasic, Ammonium Citrate Tribasic, and Potassium Phosphate Monobasic/Potassium Phosphate Dibasic.

It will be appreciated that the buffered amine oxides do not significantly alter the pH of the insecticide or fungicide products but, rather, make the pH much less likely to change based on the buffer capacity of the buffer additives.

A series of tests were performed in the United States in order to determine the effectiveness of a solution of the present invention combining an insecticide with a buffered amine oxide and the effectiveness of a solution of the present invention combining a fungicide with a buffered amine oxide.

TABLES 1-3 describe, respectively, describe the buffer systems employed in the North American experiments reported in TABLES 4 and 5, with TABLE 2 referring to the experimental method and TABLE 4 showing a group of buffer systems pH and total Ion strengths.

TABLE 1 recites the composition of buffer systems 3-4 that were used in the studies. Buffer systems 3-4 were prepared by dissolving the appropriate reagents into one liter of deionized water until a homogenous solution was obtained. TABLE 4 shows, in the left hand column, the number assigned to a particular buffer with column 2 containing the abbreviated name or full name of the buffers. The amount of acidic chemical per liter and basic chemical per liter appear in the next two pairs of columns.

TABLE 2 is directed toward the experimental method in preparation of the pre-blended amine oxide and buffer systems. The compositions of buffer system identifies the buffer system name in the first column with the next two columns providing identification of the acidic chemical and weight percent amount followed by the amount of basic chemical and the name. The last two columns provide the water weight percent and Barlox 12 (30% by weight amine oxide donor.)

TABLE 2 discloses the composition of pre-blended Amine Oxide and Buffer System 3 that was used in the studies. Buffer system 3 was prepared by dissolving the appropriate reagent salts in water and then adding the amine oxide donor in sufficient amount to make one liter of solution.

TABLE 2

Pre-blended Buffer System 3 Composition

| Buffer Letter | Buffer System Name (Abbreviated Name) | Acidic Chemical Amount (wt %) | Name | Basic Chemical Amount (wt %) | Name | Water Amount (wt %) | Barlox 12 (30% by weight amine oxide) Amine oxide Donor (wt %) |
|---|---|---|---|---|---|---|---|
| 3 | Potassium Phosphate Monobasic/Potassium Phosphate Dibasic (Phosphate Buffer 3) | 4.36 | Potassium Phosphate Monobasic | 3.13 | Potassium Phosphate Dibasic | 12.51 | 80.00 |

TABLE 3 shows the pH and buffer total Ion strengths (Molar) for buffer system 3.

TABLE 3

Buffer System pH and Total Ion Strengths

| Buffer No. | Buffer System Name (Abbreviated Name) | pH (Buffer System) | Buffer Total Ion Strength (Molar) |
|---|---|---|---|
| 3 | Potassium Phosphate Monobasic/Potassium Phosphate Dibasic (Phosphate Buffer 1) | 6.8 | 1.05M |
| 4 | Potassium Bicarbonate/Potassium Carbonate (Carbonate Buffer) | 10.2 | 0.995M |

Referring to TABLES 4 and 5, the columns under the heading Buffered Amine Oxide System correspond to the identification provided in TABLES 1 through 3.

In general, in the present invention, amine oxides were mixed with buffers and then added to insecticide or fungi-

TABLE 1

Buffer Systems 3, 4 Composition

| Buffer No. | Buffer System Name (Abbreviated Name) | Acidic Chemical (per liter) Amount | Name | Basic Chemical (per liter) Amount | Name |
|---|---|---|---|---|---|
| 3 | Potassium Phosphate Monobasic/Potassium Phosphate Dibasic (Phosphate Buffer 1) | 0.5 mol | Potassium Phosphate Monobasic | 0.5 mol | Potassium Phosphate Dibasic |
| 4 | Potassium Bicarbonate/Potassium Carbonate (Carbonate Buffer) | 0.5 mol | Potassium Bicarbonate | 0.5 mol | Potassium Carbonate | cide formulations. Among the preferred amine oxides were those of 12 carbon length such as that sold under the trade designation Barlox 12 and a mixture of the 12 and 18 carbon lengths sold under the trade designation Barlox 1218. The buffer solution serves to stabilize the pH at a nearly constant value in a wide variety of chemical operations.

In the present invention, the buffer system maintains a substantially constant pH when in contact with biological systems. The buffer system is an aqueous system consisting of a mixture of a weak acid in its conjugate or a weak base in its conjugate acid. One may obtain the desired buffer system by directly adding the weak acid/conjugate base or weak base/conjugate acid salts or by adding the weak acid/weak base and a strong acid/strong base in sufficient amount to form the conjugate acid/conjugate base.

The amine oxide additives may be mixed as tank blends with the insecticides or fungicides or may be incorporated into the insecticides or fungicide formulas.

TABLE 1 shows 2 different buffers, while TABLE 3 shows an amine oxide blend. TABLE 4 discloses systems wherein the appropriate reagents were dissolved in deionized water until a homogenous solution was obtained. TABLE 3 deals with the pre-blending of the amine oxide and buffer systems with the appropriate reagents salts dissolved in water and subsequently, adding the amine oxide donor. American Field Tests of Buffered Amine Oxide Additives to Fungicide and Insecticide (Tables 4 and 5)

Referring to TABLE 4 wherein a commonly used fungicide, PROPICONAZOLE was employed in tests in the amount of 50:200 PPM (parts per million) employed with and without buffered amine oxides systems 3 and 4 with some of the tests employing the 12 carbon length and others, the 1218 carbon mixture. In a preferred embodiment in 1218 on a weight basis, the 12 carbon length will be present in an amount of about 1.3 to 2.0 times the amount of 18 carbon length and in the preferred range about 1.5 to 1.8 times the amount of 18 carbon length. The tests were performed on white oak seedlings which were provided with a stem wound in which was introduced staining fungi which was of the ceratocystis variety. Staining indicates that the fungicide or other treatment did not resist growth of the fungi with the number 100 representing 100% with no inhibitions of fungi growth and the number 0 indicating 0% or 0 indicating no fungi growth.

Referring in TABLE 4 to the heading under No Buffer, it is seen that the amine oxides of both the 12 and 1218 length in concentrations of 200:1 and 400:1 did not in any way inhibit growth of the staining fungi. Considering the Propiconazole employed alone, it is seen that with 50 ppm, 100 ppm and 200 ppm, the inhibition at 50 ppm did not exist as there was 100% growth and that at 100 ppm, 80% growth was experienced, while at 200 ppm, 20% growth existed.

With continued reference to TABLE 4, the combination of the fungicide with the buffered amine oxide system No. 3,

TABLE 4

May to June 2013

| Fungicide Type Product Concentration PPM | No Buffer | | Buffered Amine Oxide System Buffer Number & Amine Oxide Donor or Letter[7] | | | | Percent of Seedlings with Staining Fungi in Stem Wound of White Oak (3, 4, 5, 8, 9) |
|---|---|---|---|---|---|---|---|
| Propiconazole[6] | | | 3 | | 4 | | |
| | 12 | 1218 | 12 | 1218 | 12 | 1218 | |
| | | | | | | | 100[1][2] |
| | 200:1 | | | | | | 100 |
| | 400:1 | | | | | | 100 |
| | | 200:1 | | | | | 100 |
| | | 400:1 | | | | | 100 |
| 200 PPM | | | | | | | 20 |
| 100 PPM | | | | | | | 80 |
| 50 PPM | | | | | | | 100 |
| 50 PPM | | | 200:1 | | | | 0 |
| 50 PPM | | | 400:1 | | | | 20 |
| 50 PPM | | | | 200:1 | | | 0 |
| 50 PPM | | | | 400:1 | | | 0 |
| | | | 200:1 | | | | 100 |
| | | | 400:1 | | | | 100 |
| | | | | 200:1 | | | 100 |
| | | | | 400:1 | | | 100 |
| 50 PPM | | | | | 200:1 | | 0 |
| 50 PPM | | | | | 400:1 | | 20 |
| 50 PPM | | | | | | 200:1 | 0 |
| 50 PPM | | | | | | 400:1 | 0 |
| | | | | | 200:1 | | 100 |
| | | | | | 400:1 | | 100 |
| | | | | | | 200:1 | 100 |
| | | | | | | 400:1 | 100 |

[1]Water control
[2]20 seedlings
(3) 20 milliliters per seedling; low volume hand spray
(4) *Quercus alba* -(white oak)
(5) May to June, Pennsylvania, USA
[6]Technical Material registered by United States EPA dissolved in 10% propylene glycol and 90% distilled water
[7]See Tables 1, 2 and 3 for buffers and amine oxides
(8) 7 days after application, a sterile razor blade wound of 2 millimeter by 10 millimeter on each seedling stem
(9) 14 days after wounding, wounds were examined for presence of staining fungi
10) Buffers and amine oxides were added to dilute solution of fungicide employing 50 ppm in the 12 carbon length combined with 50 ppm propiconazole, at 200:1 concentration, there was 0 fungal growth, and at 400:1, there was 20% growth. The same 50 ppm of the fungicide employed with 200:1 and 400:1, 1218 buffered amine oxide system No. 3, produced 0 fungal growth.

TABLE 4 shows that both the 12 and 1218 length of buffered amine oxide system No. 3 used alone at concentrations of 200:1 and 400:1 produced no fungal growth inhibition as both showed 100% staining fungi.

Considering buffered amine oxide system No. 4 when the 12 length is used in combination with 50 ppm of the fungicide, in concentration of 400:1, 20% fungal growth was experienced and in 200:1, no fungal growth was experienced. With regard to the fungicide being in 50 ppm and the 1218 carbon length, a buffered amine oxide system No. 4, as to both 200:1 and 400:1 concentration, there was 0 fungal growth.

Considering both the 12 length and 1218 length employed without the fungicide in both concentrations, 200:1 and 400:1, there was a 100% fungal growth.

The test results in TABLE 4, therefore, support the conclusion that, in the absence of a buffer, there was 100% fungal growth. In the use of 12 length amine oxide or 1218 length amine oxide alone with both buffered amine systems No. 3 and 4, there was 100% fungal growth. When, however, the combination of fungicide and the buffered amine oxide systems were employed, whether length 12 or 1218 was considered, when the concentration was 200:1, there was no fungal growth and when the concentration was 400:1, there was 20% fungal growth.

The method of testing the materials was to spray the trunk of the seedling with the particular solution being tested and 7 days after such application, creating a wound of approximately 2 millimeters by 10 millimeters on each seedling stem. Fourteen days after the wounding, the wounds were examined for the presence of staining fungi.

Referring to TABLE 5, there is shown the results of testing of an insecticide which, in this case, was permethrin, which was presented in various tests in quantities of 10 ppm to 50 ppm and 100 ppm concentrations were tested against a control with no buffer as well as buffer amine oxide systems employing 12 length carbon.

The particular solutions tested were applied to a stem of the white oak seedling using a low volume hand spray and spraying 20 milliliters per seedling. A total of 20 seedlings were tested. The use of permethrin alone in concentration of 10 ppm resulted in 80% gypsy moth caterpillar damage. At permethrin concentration of 50 ppm, the damage after one month was 30% and with 100 ppm used alone, the damage was 0. When buffered amine oxide system No. 3 was employed in concentrations of 400:1 with 10 ppm of the insecticide, the gypsy moth caterpillar damage was 10% and when a concentration of 200:1 was employed with 10 ppm insecticide, the damage was 0. This shows that a much smaller amount of insecticide was needed to achieve 0 damage when was used in combination with the buffered amine oxide system which created a desired synergistic effect. If less than 50 percent of the leaf mass was eaten, this shows successful inhibition of gypsy moth damage.

Using buffered amine oxide system No. 3 alone in concentrations of 400:1 and 200:1 resulted in 100% gypsy moth caterpillar damage after one month.

Using buffered amine oxide system No. 4 in combination with 10 ppm of the insecticide, reduce the gypsy moth caterpillar damage to 10% when using a concentration of 400:1 and to 0 when using a concentration of 200:1.

Using buffered amine oxide system No. 4 without the insecticide resulted in 100% gypsy moth caterpillar damage.

The foregoing tests show that neither buffered amine oxide system 3 nor 4 in concentrations of 200:1 and 400:1 produced any measurable difference in gypsy moth caterpillar damage over the control which had neither insecticide nor buffered amine oxide systems. When, however, the

TABLE 5

May to June 2013

| Insecticide Type Product Concentration PPM | No Buffer | Buffered Amine Oxide System Buffer Number & Amine Oxide Donor or Letter[7][9] | | Percent Gypsy Moth Catepillar Damage[5][8] to White Oak[4] 1 Month After Application(3) |
|---|---|---|---|---|
| Permethrin[6] | | 3 | 4 | |
| | 12 | 12 | 12 | |
| | | | | 100[1][2] |
| | 200:1 | | | 100 |
| | 400:1 | | | 100 |
| 100 PPM | | | | 0 |
| 50 PPM | | | | 30 |
| 10 PPM | | | | 80 |
| 10 PPM | | 200:1 | | 0 |
| 10 PPM | | 400:1 | | 10 |
| | | 200:1 | | 100 |
| | | 400:1 | | 100 |
| 10 PPM | | | 200:1 | 0 |
| 10 PPM | | | 400:1 | 10 |
| | | | 200:1 | 100 |
| | | | 400:1 | 100 |

[1]Water control
[2]20 seedlings
(3)20 milliliters per seedling; low volume hand spray
[4]*Quercus alba*
[5]May-June, Pennsylvania, USA
[6]Commercial concentrate containing 38.4 percent Permethrin
[7]See Tables 1, 2 and 3 for buffers and amine oxides
[8]Greater than 50% of leaf mass eaten
[9]Buffers and amine oxides were added to dilute solution of insecticide buffered amine oxide systems 3 and 4 were employed with insecticide concentrations of 10 ppm, at 400:1 concentration of the 12 length carbon buffered amine oxide systems, there was only 10% gypsy moth caterpillar damage and with 200:1 concentration, there was 0 damage.

If desired, a single solution may contain both an insecticide and a fungicide.

It will be appreciated, therefore, that both in connection with fungicide tests and insecticide tests, neither the insecticide nor fungicide employed alone achieved any meaningful reduction in staining fungi or gypsy moth caterpillar in the lower concentrations of the material. Similarly, the buffered amine oxide system, when used alone, produced no significant reduction in staining fungi or gypsy moth caterpillar damage. When, however, the fungicide was used at lower parts per million in combination with the buffered amine oxide systems, there was, due to synergism, a substantial reduction or elimination of staining fungi. Similarly, when the insecticide was used in lower concentrations in combination with buffered amine oxide systems, there was substantial reduction or elimination of gypsy moth caterpillar damage.

While particular embodiments of this invention have been described herein for purposes of illustration, it will be evident to those skilled in the art that numerous variations of the details of the present invention may be made without departing from the invention as defined in the appended claims.

What is claimed is:

1. A method of resisting destruction of living plants comprising
   providing a solution having a buffered amine oxide admixed with at least one material selected from the group consisting of insecticides and fungicides, and
   applying said solution to effect synergistic protection of said living plants against said at least one of said insects and said fungi by effecting greater resistance to said plant deterioration than said buffered amine oxide and either said insecticides and said fungicides employed alone would achieve.

2. The method of claim 1 including
   employing said solution having a buffered amine oxide concentration of at least about 400:1 on a volume to volume basis based on total solution volume.

3. The method of claim 2 including
   said solution with said buffered amine oxide being present in an amount of about 400:1 to 200:1 on a volume to volume basis based on total solution.

4. The method of claim 1 including
   said solution having a fungicide present in an amount of at least about 50 ppm on a total solution weight basis.

5. The method of claim 1 including
   said solution having an insecticide present in an amount of at least about 10 ppm on a total solution weight basis.

6. The method of claim 5 including
   said solution having insecticide in an amount of about 10 to 100 ppm on a solution total weight basis.

7. The method of claim 1 including
   said buffered amine oxide having a carbon length selected from the group consisting of (a) 12 carbon length amine oxide and (b) a mixture of 12 and 18 carbon length amine oxides.

8. The method of claim 7 including
   said 12 carbon length amine oxide on a weight basis being present in an amount of about 1.3 to 2.0 times the amount of 18 carbon length amine oxide.

9. The method of claim 7 including
   said 12 carbon length amine oxide on a weight basis being present in an amount of about 1.5 to 1.8 times the amount of 18 carbon length amine oxide.

10. The method of claim 1 including said solution containing a buffered amine oxide having a pH of about 6.5 to 10.5.

11. The method of claim 10 including said solution containing a buffered amine oxide having a pH of about 7 to 9.

12. The method of claim 1 including
    said buffered amine oxide being 12 carbon length amine oxide, and a buffer amine oxide selected from the group consisting of (a) Potassium Phosphate Monobasic/Potassium Phosphate Dibasic and (b) Potassium Bicarbonate/Potassium Carbonate.

13. The method of claim 1 including
    said buffered amine oxide is Potassium Phosphate Monobasic/Potassium Phosphate Dibasic.

14. The method of claim 1 including
    said buffered amine oxide is Potassium Bicarbonate/ Potassium Carbonate.

15. The method of claim 1, including
    said buffered amine oxide having a mixture of 12 carbon length amine oxide and 18 carbon length amine oxide and said buffers selected from the group consisting of (a) Potassium Phosphate Monobasic/Potassium Phosphate Dibasic and (b) Potassium Bicarbonate/Potassium Carbonate, and said buffered amine oxide having a concentration of about 200:1 to 400:1 on a volume to volume basis.

* * * * *

UNITED STATES PATENT AND TRADEMARK OFFICE
CERTIFICATE OF CORRECTION

PATENT NO. : 10,278,386 B2
APPLICATION NO. : 15/079478
DATED : May 7, 2019
INVENTOR(S) : Hans A. Ward et al.

It is certified that error appears in the above-identified patent and that said Letters Patent is hereby corrected as shown below:

In the Specification

Column 1, immediately below the title, please add the following:
--CROSS-REFERENCE TO RELATED APPLICATION
This application is a divisional of, and claims priority under 35.U.S.C. § 120 from United States Patent Application Serial No. 14/674,465, filed March 31, 2015, entitled SOLUTIONS FOR ENHANCING THE EFFECTIVENESS OF INSECTICIDES AND FUNGICIDES ON LIVING PLANTS AND RELATED METHODS, the contents of which are incorporated herein by reference.--.
Column 3, Line 39, "describe, respectively, describe" should read --describe, respectively,--.

Signed and Sealed this
Thirtieth Day of July, 2019

Andrei Iancu
*Director of the United States Patent and Trademark Office*